United States Patent
Hyde (10) Patent No.: US 10,117,375 B2
(45) Date of Patent: Nov. 6, 2018

(54) TRIGGERABLE SUPPORT PACKAGE FOR SEEDS

(71) Applicant: Elwha LLC, Bellevue, WA (US)

(72) Inventor: Roderick A. Hyde, Redmond, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 15/333,621

(22) Filed: Oct. 25, 2016

(65) Prior Publication Data

US 2017/0034992 A1 Feb. 9, 2017

Related U.S. Application Data (63) Continuation of application No. 13/955,884, filed on Jul. 31, 2013, now Pat. No. 9,485,985.

(51) Int. Cl.

| | | |
|---|---|---|
| A01C 1/00 | (2006.01) | |
| A01C 21/00 | (2006.01) | |
| A01C 1/06 | (2006.01) | |
| A01G 25/16 | (2006.01) | |
| A01G 25/00 | (2006.01) | |
| A01N 25/00 | (2006.01) | |
| C05G 3/00 | (2006.01) | |
| G06K 7/10 | (2006.01) | |
| H04Q 9/00 | (2006.01) | |
| A01G 22/00 | (2018.01) | |

(52) U.S. Cl.
CPC .............. *A01C 1/06* (2013.01); *A01C 1/00* (2013.01); *A01C 21/00* (2013.01); *A01C 21/007* (2013.01); *A01G 22/00* (2018.02); *A01G 25/165* (2013.01); *A01G 25/167* (2013.01); *A01N 25/00* (2013.01); *C05G 3/0052* (2013.01); *G06K 7/10475* (2013.01); *H04Q 9/00* (2013.01)

(58) Field of Classification Search
CPC ......... A01C 1/00; A01C 21/00; A01C 21/007; A01C 1/06; A01G 1/001; A01G 1/00; A01G 25/165; A01G 25/16; A01G 25/00; A01G 25/167; A01G 22/00; A01N 25/00; C05G 3/0052; C05G 3/0005; C05G 3/00; G06K 7/10475; G06K 7/10366; G06K 7/10009; G06K 7/10; G06K 7/00
See application file for complete search history.

(56) References Cited

U.S. PATENT DOCUMENTS

| | | | |
|---|---|---|---|
| 5,202,675 A | 4/1993 | Tokimoto et al. | |
| 5,317,834 A | 6/1994 | Anderson | |
| 5,518,995 A | 5/1996 | Abrams et al. | |

(Continued)

FOREIGN PATENT DOCUMENTS

| | | |
|---|---|---|
| JP | 2009-284199 | 12/2009 |
| WO | WO 2006/039283 | 4/2006 |
| WO | WO 2011/133765 | 10/2011 |

OTHER PUBLICATIONS

PCT International Search Report, International Application No. PCT/US2014/048030, dated Nov. 7, 2014, pp. 1-3.

*Primary Examiner* — Christopher J. Novosad
(74) *Attorney, Agent, or Firm* — Foley & Lardner LLP (57) ABSTRACT

A system for enhancement of crop production includes a triggerable seed support package. The triggerable seed support package has a payload including seed enhancement material, where the payload is configured to be released in response to a trigger.

13 Claims, 9 Drawing Sheets

(56) References Cited

U.S. PATENT DOCUMENTS

| | | | |
|---|---|---|---|
| 5,652,196 | A | 7/1997 | Luthra et al. |
| 5,794,550 | A | 8/1998 | Chadwich |
| 6,088,957 | A | 7/2000 | Kazemzadeh |
| 6,199,318 | B1 | 3/2001 | Stewart et al. |
| 6,230,438 | B1 | 5/2001 | Zaychuk et al. |
| 8,209,902 | B2 | 7/2012 | Ruban et al. |
| 8,215,058 | B2 | 7/2012 | Cook |
| 9,485,985 | B2 * | 11/2016 | Hyde .................. H04Q 9/00 |
| 2004/0078068 | A1 | 4/2004 | Neuberger |
| 2005/0086274 | A1 | 4/2005 | Mori |
| 2006/0150489 | A1 | 7/2006 | Legro et al. |
| 2008/0056622 | A1 * | 3/2008 | Austreng ........... B65D 33/1691 383/5 |
| 2008/0072494 | A1 | 3/2008 | Stoner et al. |
| 2008/0283548 | A1 | 11/2008 | Miller |
| 2009/0227451 | A1 | 9/2009 | Rose et al. |
| 2009/0231101 | A1 | 9/2009 | Hyde et al. |
| 2010/0235949 | A1 | 9/2010 | Sluijter et al. |
| 2011/0000411 | A1 | 1/2011 | Ruban et al. |
| 2011/0041401 | A1 | 2/2011 | Cook |

* cited by examiner

TRIGGERABLE SUPPORT PACKAGE FOR SEEDS

CROSS-REFERENCE TO RELATED PATENT APPLICATIONS

This application is a continuation of U.S. patent application Ser. No. 13/955,884, entitled "TRIGGERABLE SUPPORT PACKAGE FOR SEEDS," filed Jul. 31, 2013, which is currently copending and incorporated herein by reference in its entirety and for all purposes.

BACKGROUND

Increasing populations and diminishing farm lands place increasing demands on agricultural efficiency. The successful cultivation of a crop is dependent on numerous variables, and it has long been the goal of farmers to enhance the growth of plants in order to increase crop quantity and quality. Farmers deliver nutrients to planted seeds in order to provide a more uniform germination rate and a more consistent overall yields.

SUMMARY

One embodiment relates to a system for enhancement of crop production including a triggerable seed support package. The triggerable seed support package comprises a payload including seed enhancement material, where the payload is configured to be released in response to a trigger.

Another embodiment relates to a method of enhancing crop production. The method includes planting a triggerable seed support package comprising a payload including seed enhancement material, where the payload is configured to be released in response to a trigger; and applying the trigger to an area of the planted triggerable seed support package in order to trigger a release of the payload.

Another embodiment relates to a system for enhancement of crop production including a triggerable seed support package. The triggerable seed support package includes a sensor configured to generate sensor data, a payload including seed enhancement material, wherein the payload is configured to be released in response to a trigger, and a processing circuit configured to detect a trigger based on the sensor data and control a release of the payload based on the trigger.

Another embodiment relates to a method of enhancing crop production. The method includes planting a triggerable seed support package and applying a trigger to an area of the planted triggerable seed support package in order to trigger the release of the payload. The triggerable seed support package includes a sensor configured to generate sensor data, a payload including seed enhancement material, wherein the payload is configured to be released in response to a trigger, and a processing circuit configured to detect the trigger based on the sensor data and control a release of the payload based on the trigger.

Another embodiment relates to a non-transitory computer-readable medium having instructions stored thereon, the instructions forming a program executable by a processing circuit to cause the processing circuit to perform operations including analyzing sensor data from a sensor of a triggerable seed support package, detecting a trigger based on the sensor data, and controlling the release of a payload of the seed support package based on the trigger. The seed support package includes the sensor configured to generate the sensor data, the payload including seed enhancement material, wherein the payload is configured to be released in response to the trigger, and the processing circuit.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring generally to the figures, various embodiments for triggerable seed support packages are shown and described. Crop production may be enhanced by using seed support packages that are planted with the seed. Such seed support packages may contain a single seed or multiple seeds, or may be configured to support an external seed or seeds. The seed support packages include a payload of seed enhancement material to be delivered to planted seed in response to a trigger. Various triggers may be used to control the release of a payload, as will be discussed in detail herein. The seed support packages may be designed from a material that is triggerable to cause the release of seed enhancement material on command (or in response to a certain condition). Alternatively, a processing circuit and sensor may be used within the seed support package to allow control of the delivery of the seed enhancement material. By controlling the release of a payload, the seed enhancement material within the payload (e.g., fertilizers, micronutrients, probiotics, chemicals, plant hormones, etc.) may be discharged to initiate or aid the germination of a planted seed, or to support plant development. As a general example, the sensor may be a radiofrequency (RF) sensor, and the trigger may be a radiofrequency signal that is transmitted over a field where such a seed support package has been planted along with seed. Upon transmission of the radiofrequency signal trigger, the sensor may detect the radiofrequency trigger signal and the processing circuit may initiate the release of seed enhancement material, thereby allowing a farmer to cause the seed to germinate on command. Many other triggers and sensor configurations may also be utilized in such a seed support package.

Figure 1:
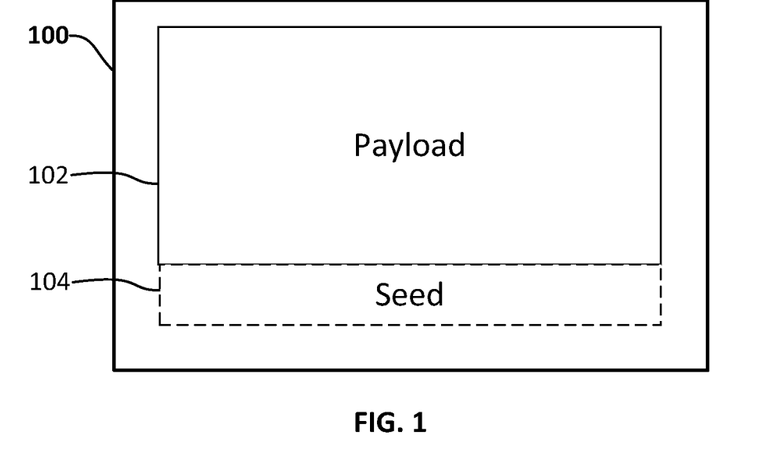
FIG. 1 is a block diagram of a triggerable seed support package according to one embodiment.

Referring to FIG. 1, a block diagram of triggerable seed support package 100 is shown. According to one embodiment, seed support package 100 includes payload 102. Payload 102 includes seed enhancement material and is generally configured to be released in response to a trigger. Payload 102 may also include other materials aside from seed enhancement material (e.g., binders, preservatives, reactive agents, etc.). Seed support package 100 includes all components necessary to release payload 102. In one embodiment, seed support package 100 includes a containment barrier or a compartment that may be opened or closed in response to the trigger. In this manner, a seed or soil may be allowed access to the payload through the opened containment barrier. In one embodiment, seed support package 100 may comprise packaging material designed to enclose payload 102. In another embodiment, the packaging material of seed support package 100 may integrate payload 102 therethrough. For example, seed enhancement material of payload 102 may be distributed throughout the outer packaging material of seed support package 100. The seed enhancement material may include substances used to initiate germination of a seed, or to initiate/support/retard subsequent events of plant development. For example, the seed enhancement material may include fertilizers, micronutrients, probiotics, chemicals, plant hormones, etc. For example, the fertilizers may be organic or inorganic compounds, may be in pellet or liquid format, and may be formulated for prompt or controlled release. The fertilizers may include at least one of nitrogen, phosphorus, potassium, calcium, magnesium, or sulfur. The fertilizers may include compounds such as ammonium nitrate, urea, potassium chloride, or phosphoric acid. As an example, the micronutrients may include at least one of the elements boron, chlorine, copper, iron, manganese, molybdenum, zinc, or nickel. The micronutrients may be in elemental form, or may be formulated as molecular compounds. As an example, the probiotics may include nitrogen fixing bacteria, phosphate solubilizers, methylobacteria, rhizobacteria, *bacillus subtilis, azospirillum, lactobacillus*, or the like. A variety of plant probiotics and their effects are described in *Bacteria in Agrobiology: Plant Probiotics* by Dinesh Maheshwari, ISBN 978-3642275142 (2012). For example, the plant hormones may include abscisic acid, auxins, cytokinins, ethylene, gibberellins, brassinosteroids, jasmonates, plant peptides, polyamines, nitric oxide donors, or karrikins, or the like. In one embodiment, seed support package 100 is configured to include seed 104. Seed 104 may be a single seed, multiple seeds, seedling, etc. In another embodiment, seed support package 100 is configured to support a seed, multiple seeds, or seedling external to seed support package 100.

Various triggers may be utilized to control the release of payload 102. In one embodiment, packaging material of seed support package 100 is reactive to a trigger material (e.g., sensitive to moisture, etc.). For example, seed support package 100 may dissolve or break apart due to soil moisture and payload 102 may be released. In this manner, water may be delivered to a field in which seed support package 100 has been placed to trigger the release of release payload 102. In one embodiment, packaging material of seed support package 100 is sensitive to a certain chemical. For example, seed support package 100 may dissolve or break apart due to a reaction between the packaging material and the trigger chemical. In this manner, the chemical may sprayed across a field in which seed support package 100 is planted to trigger the release of release payload 102 as the chemical penetrates seed support package 100.

In another embodiment, seed support package 100 may be configured to include a time-based trigger. For example, seed support package 100 may be comprised of a material configured to break down over a certain period of time. In another embodiment, seed support package 100 may be configured to include a mechanical time-based trigger. The trigger may cause the release of payload 102 at a specified time, or after a certain amount of time has elapsed. For example, the trigger may cause seed support package 100 to break apart and thereby release payload 102. As another example, the trigger may cause a compartment within seed support package 100 to open and thereby release payload 102. Multiple seed support packages 100 may be planted in a field along with seeds, and may be configured to release payload 102 at a synchronized time across the field. In this manner, the germination of seeds of a crop may be initiated in a coordinated fashion.

Figure 2:
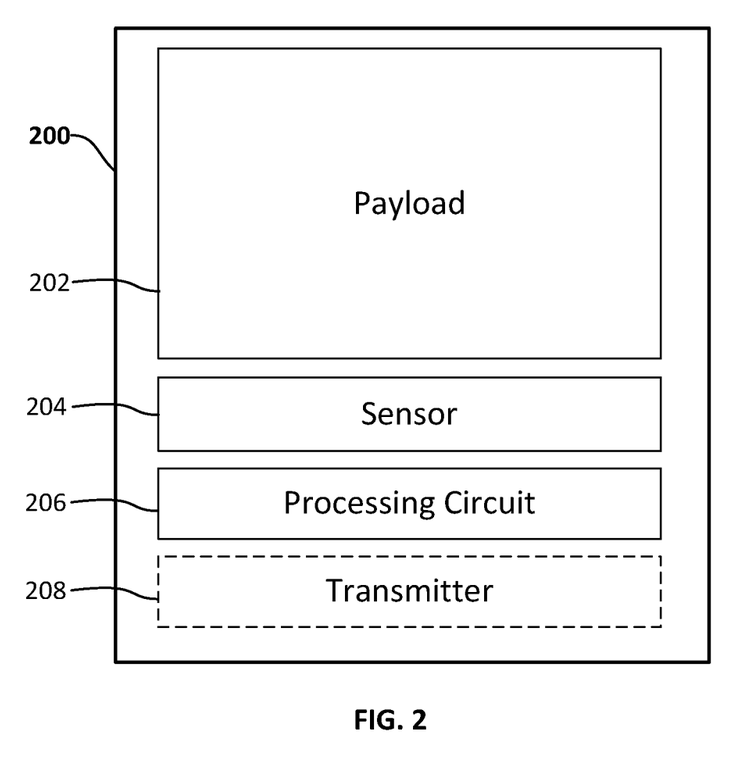
FIG. 2 is a block diagram of a triggerable seed support package according to one embodiment.

Referring to FIG. 2, a block diagram of triggerable seed support package 200 is shown. According to one embodiment, seed support package 200 includes payload 202, sensor 204, and processing circuit 206. Seed support package 200 includes all components necessary to release payload 202 and may be comprised of material as discussed for seed support package 100 of FIG. 1. Payload 202 includes seed enhancement material and is configured to be released in response to a trigger. Sensor 204 includes various sensing components that provide data to processing circuit 206. For example, sensor 204 may include a radiofrequency sensor, a temperature sensor, a moisture sensor, a chemical sensor, a light sensor, a vibration sensor, or any combination of sensors, etc. Processing circuit 206 is generally configured to analyze the sensor data to trigger the release of payload 202. In one embodiment, seed support package 200 includes a transmitter 208. Transmitter 208 includes components necessary to transmit reporting data (e.g., feedback provided to a control device, etc.). For example, transmitter 208 may include a radiofrequency transmitter, and reporting data may include data provided by sensor 204 or data related to a release of payload 202, etc. Multiple triggerable seed support packages 200 may be planted with seeds of a crop and may be configured to respond to a single trigger. Alternatively, seed support packages 200 may be configured to response to a unique trigger, or to a trigger corresponding to a particular group of seeds, area of a field, etc. By adjusting the triggering properties of seed support packages 200, a grower can control and synchronize the deployment of payload 202 for an entire crop, specific areas of a crop, specific groups of seeds, a specific seed, or any combination as desired by the grower. In one embodiment seed support package 200 includes a power supply (e.g., a battery, a fuel cell, a solar cell, etc.) in order to provide electrical power to support the release of payload 202, the operation of sensor 204, processing circuit 206, or transmitter 208.

Figure 3:
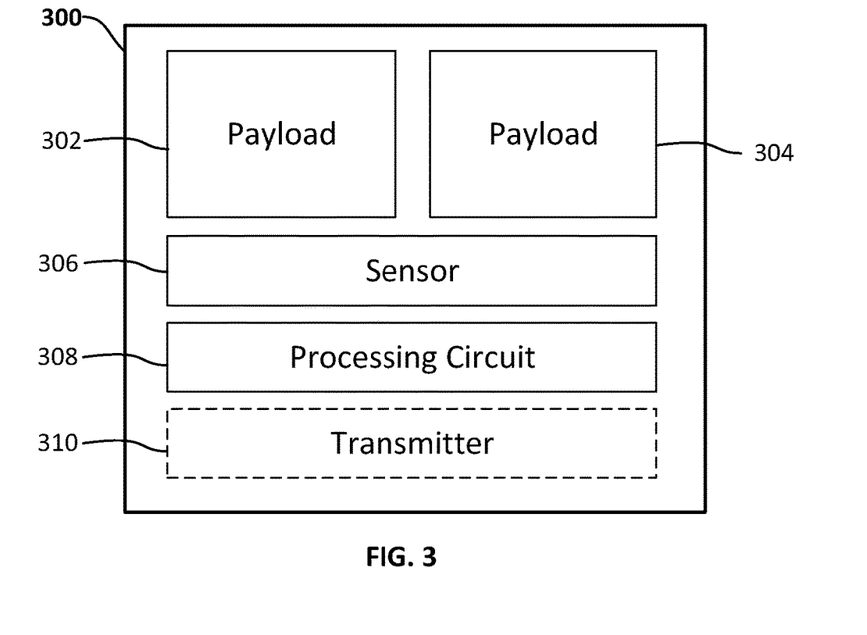
FIG. 3 is a block diagram of a triggerable seed support package according to one embodiment.

Referring to FIG. 3, a block diagram of triggerable seed support package 300 is shown. According to an embodiment, seed support package 300 includes multiple payloads (depicted as payload 302 and payload 304). Although shown as including two payloads, seed support package 300 may be configured to include any number of payloads. Payloads 302 and 304 of seed support package 300 may be stored together or separately (e.g., in the same compartment or separate compartments), and payloads 302 and 304 may be configured to be triggered by the same trigger or different triggers. For example, both payload 302 and payload 304 may be configured to be released in response to a single trigger. As another example, payload 302 may include a first seed enhancement material and configured to release in response to a first trigger. Payload 304 may include a second seed enhancement material configured to be released in response to a second trigger. Sensor 306 includes various sensing components that provide data to processing circuit 308. Processing circuit 308 is generally configured to analyze the sensor data to trigger and control the release of payloads 302 and 304. In one embodiment, seed support package 300 includes a transmitter 310. Transmitter 310 includes components necessary to transmit reporting data (e.g., to a control center, etc.). For example, transmitter 310 may include a radiofrequency transmitter, and reporting data may include data provided by sensor 306 or data related to a release of payloads 302 and 304, etc.

Figure 4:
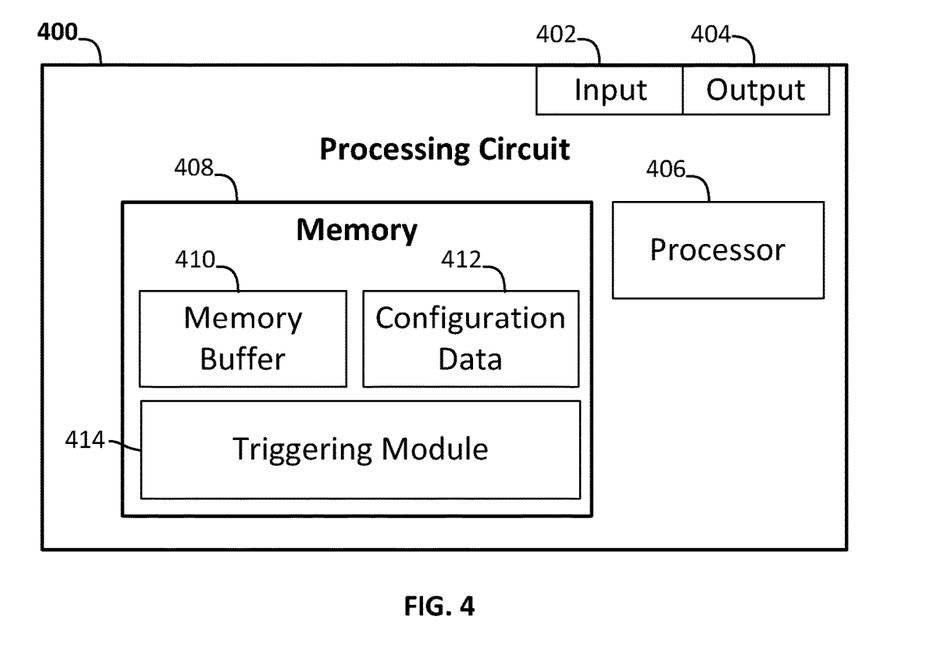
FIG. 4 is a block diagram of a processing circuit according to one embodiment.

Referring to FIG. 4, a detailed block diagram of processing circuit 400 for completing the systems and methods of the present disclosure is shown according to one embodiment. Processing circuit 400 is generally configured to accept input from a sensor device. Processing circuit 400 is further configured to receive configuration data. Input data may be accepted continuously or periodically. Processing circuit 400 uses the input data to detect and determine a trigger to control the release of the payload of a seed support package. Processing circuit 400 may generate the signals necessary to control mechanical compartments or switches, initiate chemical reactions, and generally control the release of a payload. Processing circuit 400 may generate reporting data and format the data to be transmitted. In controlling the release of a payload of a seed support package, processing circuit 400 may make use of machine learning, artificial intelligence, interactions with databases and database table lookups, pattern recognition and logging, intelligent control, neural networks, fuzzy logic, etc. Processing circuit 400 further includes input 402 and output 404. Input 402 is configured to receive a data stream (e.g., a digital or analog stream of data) and configuration information. Output 404 is configured to output data for transmission or for use in a configuration process of a seed support package, and to output data to components of the systems as described herein.

According to one embodiment, processing circuit 400 includes processor 406. Processor 406 may be implemented as a general-purpose processor, an application specific integrated circuit (ASIC), one or more field programmable gate arrays (FPGAs), a digital-signal-processor (DSP), a group of processing components, or other suitable electronic processing components. Processing circuit 400 also includes memory 408. Memory 408 is one or more devices (e.g., RAM, ROM, Flash Memory, hard disk storage, etc.) for storing data and/or computer code for facilitating the various processes described herein. Memory 408 may be or include non-transient volatile memory or non-volatile memory. Memory 408 may include database components, object code components, script components, or any other type of information structure for supporting the various activities and information structures described herein. Memory 408 may be communicably connected to processor 406 and include computer code or instructions for executing the processes described herein (e.g., the processes shown in FIGS. 5-11).

Memory 408 includes memory buffer 410. Memory buffer 410 is configured to receive a data stream from a sensor device (e.g. sensor 204 or sensor 306, etc.) through input 402. For example, the data may include a real-time stream of radiofrequency signal data. As another example, the data may include a stream of temperature data. As another example, the data may include a stream of moisture data from a moisture sensing device. As another example, the data may include a stream of light data from a light sensor. The data received through input 402 may be stored in memory buffer 410 until memory buffer 410 is accessed for data by the various modules of memory 408. For example, triggering module 414 can access the data that is stored in memory buffer 410. The data received through input 402 may also be immediately accessed.

Memory 408 further includes configuration data 412. Configuration data 412 includes data related to processing circuit 400. For example, configuration data 412 may include information related to interfacing with other components (e.g., sensors, mechanical switches, mechanical compartments, transmitters, etc.). This may include the command set needed to interface with a computer system used configure seed support packages having processing circuit 400. Based on data stored in configuration data 412, processing circuit 400 may format data for output via output 404, which may include formatting packet of data s for transmission via a transmitter, etc. Configuration data 412 may further include information as to how often input should be accepted from a sensor device. Configuration data 412 may include default values required to initiate a seed support package and initiate communication with sensors of the seed support package. Configuration data 412 includes data defining a trigger and/or characteristics of a triggering event. Trigger data may include required sensor data (e.g., characteristics of sensor data, maximum/minimum values, average values, durations, schedules, etc.) that must be present in order to trigger a release of a payload. Configuration data 412 further includes data to configure communication between the various components of processing circuit 400.

Memory 408 further includes triggering module 414. Triggering module 414 is configured to receive sensor data from a sensor device including a single sensor or multiple sensors (e.g., sensor 204, sensor 306, etc.), configuration information, and other data as provided by processing circuit 400. Triggering module 414 monitors data provided by the sensor device to detect a trigger as represented in the sensor data or to determine whether a triggering event has occurred. If a trigger is determined based on the sensor data, triggering module 414 controls the release of a payload of the seed support package.

In one embodiment, the sensor device includes a radiofrequency sensor configured to detect a radiofrequency signal. Triggering module 414 is configured to process data provided by the radiofrequency sensor. Triggering module 414 may analyze the sensor data to determine if a certain frequency signal has been received. In doing so, triggering module 414 may analyze various properties of the radiofrequency signal (e.g., frequency, amplitude, wavelength, etc.). If the signal includes properties defined to be the trigger (e.g., as provided by configuration data 412), triggering module 414 may initiate the release of the payload. In this embodiment, the radiofrequency signal itself may be deemed to be the trigger. As an example, configuration data 412 may specify that a 15 kHz radiofrequency signal is a trigger. Upon detecting a 15 kHz radiofrequency signal by analyzing the radiofrequency sensor data, triggering module 414 may generate the commands necessary to initiate a release of a payload. In another embodiment, triggering module 414 may be configured to control the release of multiple payloads. For example, a seed support package may include a first payload (e.g., seed enhancement material to initiate germination of a seed) configured to be triggered by a 15 kHz radiofrequency signal, and a second payload (e.g., micronutrients to aid plant development) configured to be triggered by a 25 kHz radiofrequency signal. Triggering module 414 analyzes the radiofrequency sensor data, and upon detection of a 15 kHz signal or a 25 kHz signal, triggering module 414 generates the commands necessary to initiate a release of the payload corresponding to the detected trigger signal.

In one embodiment, the radiofrequency trigger signal is encoded with data to address a specific seed support package or a group of seed support packages. Triggering module 414 analyzes and decodes the signal data from the sensor. Triggering module 414 may access configuration data 412 to determine if the signal should be ignored or accepted as a valid trigger. For example, configuration data 412 may specify a specific identification code or data for the seed support package that must be transmitted within the radiofrequency signal in order for triggering module 414 to consider the signal a valid trigger. If the code or data is present, triggering module 414 may initiate the release of the payload as discussed above. If the code or data is absent from the signal, triggering module 414 may ignore the signal. In one embodiment the radiofrequency trigger signal may be encoded with a particular action or instruction to be taken by processing circuit 400. For example, an action may include controlling a release of payload (e.g., a release rate, a release amount, etc.) or scheduling a release of payload (e.g., setting the time of the release of the payload, etc.). Processing circuit 400 may also be reprogrammed and reconfigured based on instructions included within the radiofrequency trigger signal. Triggering module 414 analyzes the signal data from the sensor and decodes the action/instruction. Triggering module 414 may generate necessary signals to initiate the specified action or to reprogram processing circuit 400 according to the instruction.

In one embodiment, the sensor device includes a temperature sensor configured to provide temperature data (e.g., the temperature of the soil, etc.). Triggering module 414 is configured to process data provided by the temperature sensor. Triggering module 414 may analyze the temperature data and compare it to values stored in configuration data 412 in order to determine whether to trigger the release of a payload. For example, configuration data 412 may specify that the trigger is a soil temperature of 65° F. In this manner, triggering module 414 may initiate the release of the payload when the temperature data indicates a soil temperature of at least 65° F. In another example, configuration data 412 may specify that a certain temperature and duration of time may trigger the release of the payload. In another example, configuration data 412 may specify that an average temperature over a duration of time may trigger the release of the payload. In another example, configuration data 412 may specify a temperature range that may trigger the release of the payload. Multiple triggers and conditions may be specified in configuration data 412.

In one embodiment, the sensor device includes a light sensor configured to provide light data (e.g., characteristics of light propagating onto or into the soil, etc.). Triggering module 414 is configured to process the data provided by the light sensor. Triggering module 414 may analyze the light data and compare it to values stored in configuration data 412 to determine whether to trigger and release a payload. For example, configuration data 412 may specify that a certain level of light is required to trigger the release of the payload. As another example, configuration data 412 may specify that a certain level of light is required for a duration of time in order to trigger the release of the payload.

In one embodiment, the sensor device includes a chemical sensor configured to provide data related to detected chemicals (e.g., chemicals within the soil, etc.). Triggering module 414 may analyze the sensor data and compare it to values stored in configuration data 412 to determine whether to trigger and release a payload. For example, configuration data 412 may specify that a certain chemical must be present within the soil to trigger the payload. In this manner, a grower who is utilizing a seed support package including processing circuit 400 may initiate the germination of a seed by spraying the field with the trigger chemical (e.g., a nutrient, a fertilizers, an activator, etc.). Upon detection of the chemical by triggering module 414, the payload containing seed enhancement material may be released by triggering module 414.

In one embodiment, the sensor device includes a moisture sensor configured to provide data related to moisture levels (e.g., moisture of the soil, etc.). Triggering module 414 may analyze the sensor data and compare it to values stored in configuration data 412 to determine whether to trigger the release of a payload. For example, configuration data 412 may specify that a trigger is a certain level of moisture must present within the soil. As another example, configuration data 412 may specify that a certain level of soil moisture must be present for a certain duration of time in order to trigger the release of the payload. In this manner, a grower utilizing a seed support package of this embodiment may trigger the germination of a seed by watering the field until a desired moisture level is reached. As another example, a grower may plant seed support packages of this embodiment in anticipation of rain (e.g., based on a weather forecast, etc.). After a sufficient rain shower has occurred, triggering module 414 may automatically control the release of the payload in order to trigger the germination of a seed within the newly moist soil.

In one embodiment, the sensor device includes a vibration sensor configured to detect a vibration signal. The vibration may be a seismic signal (e.g., detected by a sub-surface vibration sensor). The vibration may be an audio signal (e.g., detected by a above surface vibration sensor). Triggering module 414 is configured to process data provided by the vibration sensor. Triggering module 414 may analyze the sensor data to determine if a certain frequency signal has been received. In doing so, triggering module 414 may analyze various properties of the vibration signal (e.g., frequency, amplitude, wavelength, longitudinal/shear mode, etc.). If the signal includes properties defined to be the trigger (e.g., as provided by configuration data 412), triggering module 414 may initiate the release of the payload. In this embodiment, the vibration signal itself may be deemed to be the trigger. As an example, configuration data 412 may specify that a 3 Hz vibration signal is a trigger. Upon detecting a 3 Hz vibration signal by analyzing the vibration sensor data, triggering module 414 may generate the commands necessary to initiate a release of a payload. In another embodiment, triggering module 414 may be configured to control the release of multiple payloads. For example, a seed support package may include a first payload (e.g., seed enhancement material to initiate germination of a seed) configured to be triggered by a 3 Hz vibration signal, and a second payload (e.g., micronutrients to aid plant development) configured to be triggered by a 1 Hz vibration signal. Triggering module 414 analyzes the vibration sensor data, and upon detection of a 3 Hz signal or a 1 Hz signal, triggering module 414 generates the commands necessary to initiate a release of the payload corresponding to the detected trigger signal.

In one embodiment, the vibration trigger signal is encoded with data to address a specific seed support package or a group of seed support packages. Triggering module 414 analyzes and decodes the signal data from the sensor. Triggering module 414 may access configuration data 412 to determine if the signal should be ignored or accepted as a valid trigger. For example, configuration data 412 may specify a specific identification code or data for the seed support package that must be transmitted within the vibration signal in order for triggering module 414 to consider the signal a valid trigger. If the code or data is present, triggering module 414 may initiate the release of the payload as discussed herein. If the code or data is absent from the signal, triggering module 414 may ignore the signal. In one embodiment the vibration trigger signal may be encoded with a particular action or instruction to be taken by processing circuit 400. For example, an action may include controlling a release of payload (e.g., a release rate, a release amount, etc.) or scheduling a release of payload (e.g., setting the time of the release of the payload, etc.). Processing circuit 400 may also be reprogrammed and reconfigured based on instructions included within the vibration trigger signal. Triggering module 414 analyzes the signal data from the sensor and decodes the action/instruction. Triggering module 414 may generate necessary signals to initiate the specified action or to reprogram processing circuit 400 according to the instruction.

In one embodiment, the sensor device is separate (e.g., off-board, etc.) from the seed support package including processing circuit 400. The off-board sensor device may be linked to the seed support package wirelessly (e.g., via the radiofrequency signal, etc.). The off-board sensor device may be linked to the seed support package by a communications cable (e.g., via an electrical conductor, an optical fiber, etc.). The off-board sensor may be located above ground (e.g., a light sensor, an audio vibration sensor, a radiofrequency sensor). The off-board sensor may comprise an antenna (e.g., for radiofrequency signals) which is electrically connected to the seed support package, wherein part or all of the antenna protrudes above ground. The off-board sensor device may be linked to a group of seed support packages, providing triggering information to them. Upon reception of the off-board sensor data, triggering module 414 may analyze the data as discussed with respect to the various embodiments including on-board sensors. For example, the off-board sensor data may include moisture data from a moisture probe device installed at a particular location or depth in the field. As another example, the off-board sensor data may include temperature data from a temperature sensing device installed at a particular location or depth in the field. As another example, the off-board sensor data may include data from a chemical sensing device installed at a particular location or depth in the field. Triggering module 414 may analyze the off-board sensor data and compare it to configuration data 412 in determining whether to trigger the release of a payload.

In one embodiment the processing circuit 400 is separate from the seed support package 400. The processing circuit may be physically connected to an off-board sensor, or may be physically separate from the sensor (whether the sensor is on-board or off-board the seed support package). The off-board processing circuit may be linked to the seed support package or sensor wirelessly (e.g., via the radiofrequency signal, etc.). The off-board processing circuit may be linked to the seed support package or sensor by a communications cable (e.g., via an electrical conductor, an optical fiber, etc.). The off-board processing circuit may be linked to a group of seed support packages, providing triggering commands to them.

In any of the embodiments described herein, a trigger or triggering event may be based on a function of sensor values from one or more sensors. Further, processing circuit 400 may be configured to store sensor values in order to maintain a history of the values. Configuration data 412 may specify that a certain trend or progression of sensor values must be present in order to trigger the release of a payload. Accordingly, any of the triggers or triggering events discussed herein may be based on historical sensor data.

Figure 5:
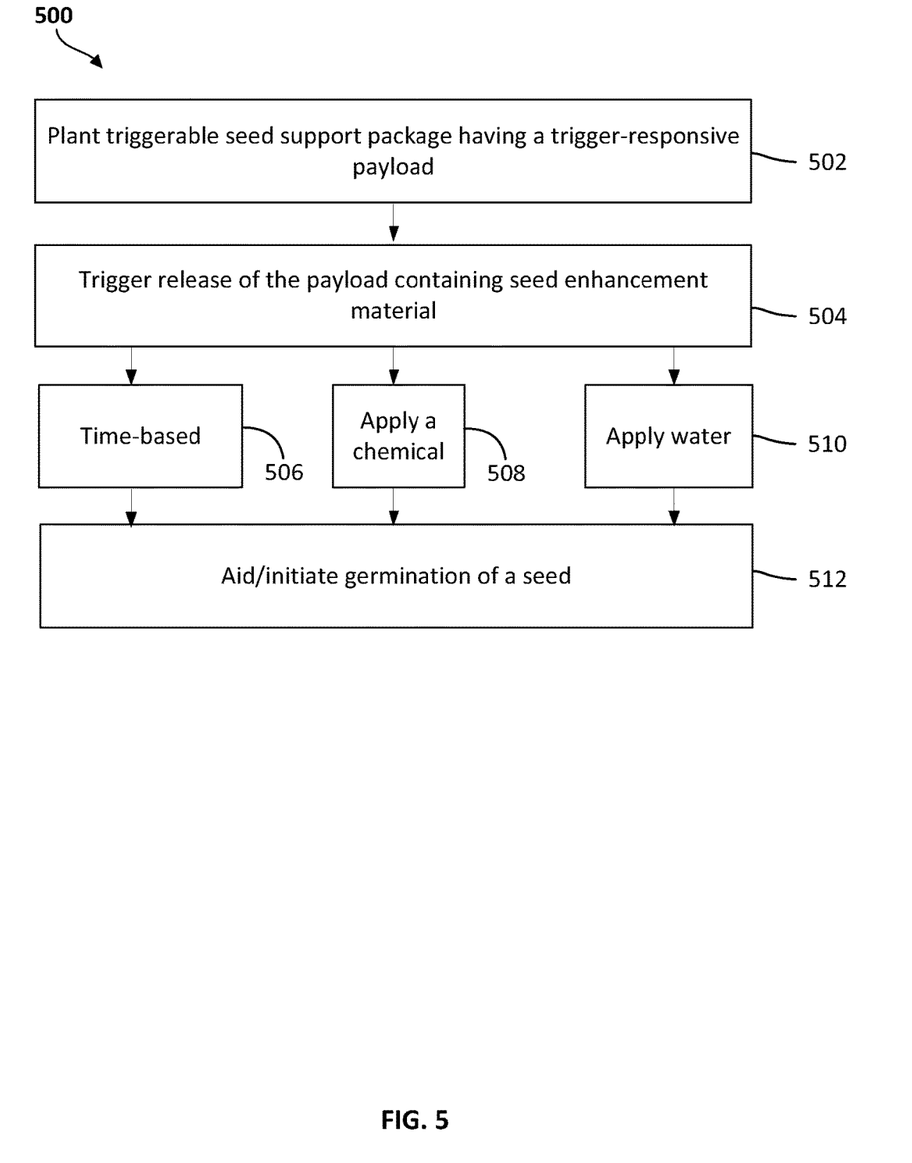
FIG. 5 is a flowchart of a process for enhancing crop production according to one embodiment.

Referring to FIG. 5, a flow diagram of a process 500 for enhancing crop production is shown, according to one embodiment. In alternative embodiments, fewer, additional, and/or different actions may be performed. Also, the use of a flow diagram is not meant to be limiting with respect to the order of actions performed. A triggerable seed support package having a trigger-responsive payload is planted (502). The seed support package may contain a seed or multiple seeds, or be configured to support an external seed or seeds. The payload of the seed support package is triggered to release seed enhancement material (504). The trigger may be time-based (506) (e.g., through breakdown of packaging containing the payload, a time-based mechanical triggering device, etc.). The trigger may also be a chemical applied to the field (e.g., for a seed support packages constructed from a chemically-sensitive material, etc.) (508). The trigger may also be a water applied to the field (e.g., for a seed support packages constructed from a moisture-sensitive material, etc.) (510). The released seed enhancement material aids or initiates germination of a seed (512). Alternatively, the payload may include seed enhancement material configured to support plant growth or initiate/retard plant developmental events. For example, seed enhancement material may be configured to prevent a seedling from rotting.

Figure 6:
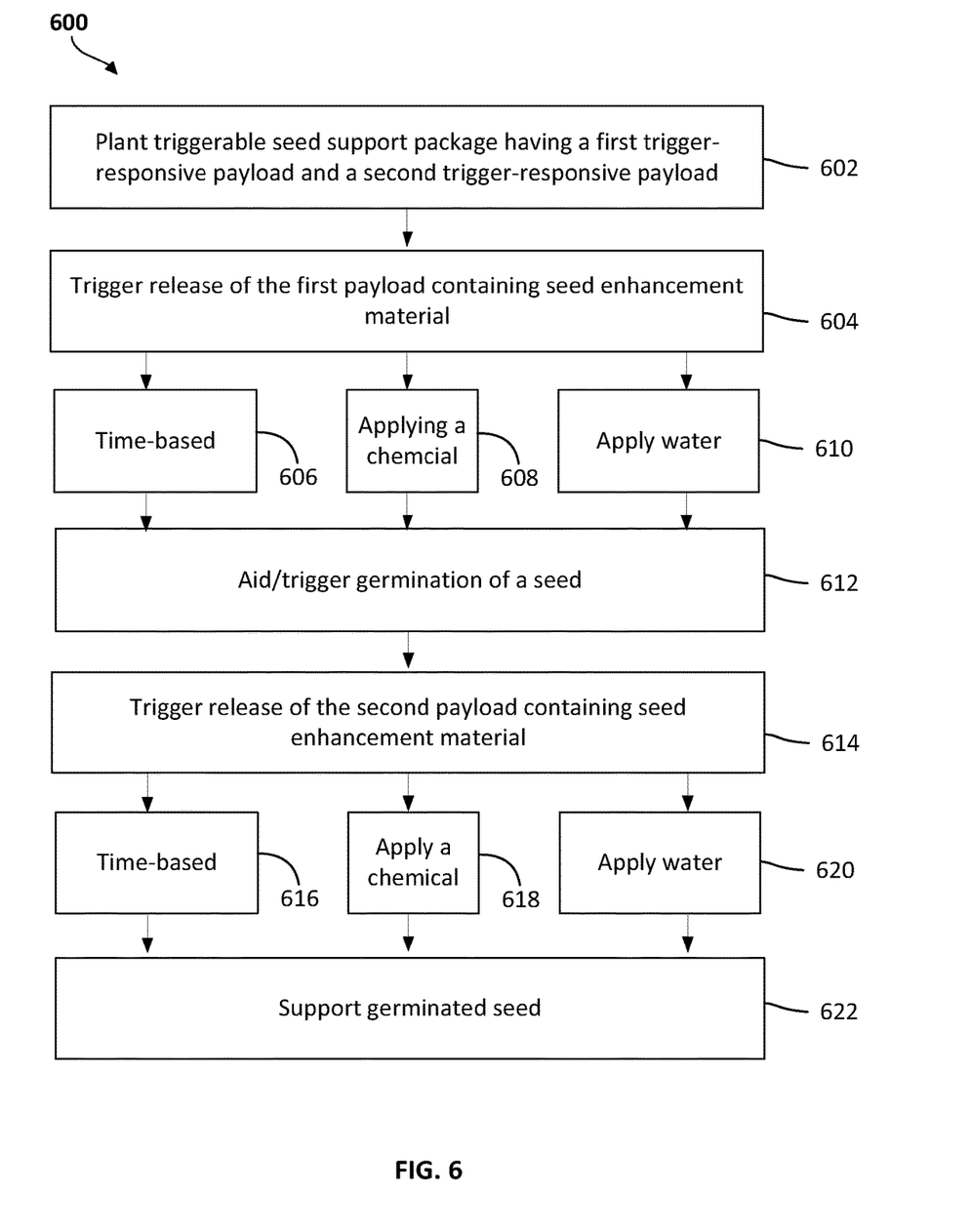
FIG. 6 is a flowchart of a process for enhancing crop production according to one embodiment.

Referring to FIG. 6, a flow diagram of a process 600 for enhancing crop production is shown, according to one embodiment. In alternative embodiments, fewer, additional, and/or different actions may be performed. Also, the use of a flow diagram is not meant to be limiting with respect to the order of actions performed. A triggerable seed support package having a first trigger-responsive payload and a second trigger-responsive payload is planted (602). The seed support package may contain a seed or multiple seeds, or be configured to support an external seed or seeds. The first payload of the seed support package is triggered to release seed enhancement material (604). The first trigger may be time-based (606), chemical-based (608), or moisture-based (610). The first payload includes seed enhancement material configured to aid or initiate germination of a seed (612). The second payload of the seed support package is then triggered to release seed enhancement material (614). The seed enhancement material of the second payload may include the same or different material than the first payload, and may be selected to initiate/retard a particular plant developmental event. The second trigger may be time-based (616), chemical-based (618), or moisture-based (620). The release of the second seed enhancement material may support the growth of the previously germinated seed (622).

Figure 7:
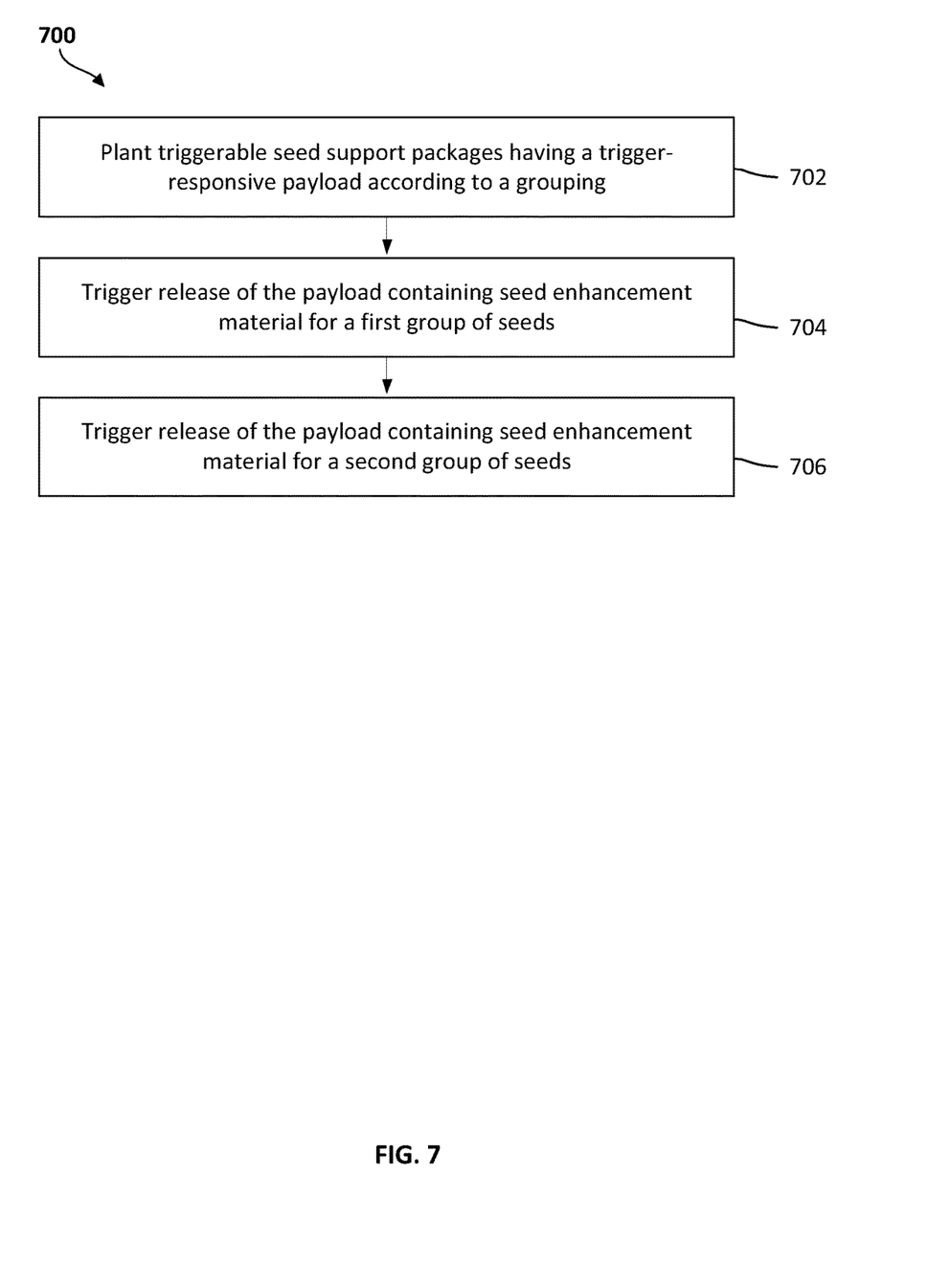
FIG. 7 is a flowchart of a process for enhancing crop production according to one embodiment.

Referring to FIG. 7, a flow diagram of a process 700 for enhancing crop production is shown, according to one embodiment. In alternative embodiments, fewer, additional, and/or different actions may be performed. Also, the use of a flow diagram is not meant to be limiting with respect to the order of actions performed. Triggerable seed support packages having trigger-responsive payloads are planted according to a grouping (702). Different triggers may be used to control the release of payloads of different seed support packages. For example, a first group of seed support packages (and seeds) may be configured to respond to a first trigger, and a second group of seed support packages (and seeds) may be configured to respond to a second trigger. The payloads of the seed support packages of the first group are triggered to release seed enhancement material for the first group of seeds (704). The payloads of the seed support packages of the second group are triggered to release seed enhancement material for the second group of seeds (706).

Figure 8:
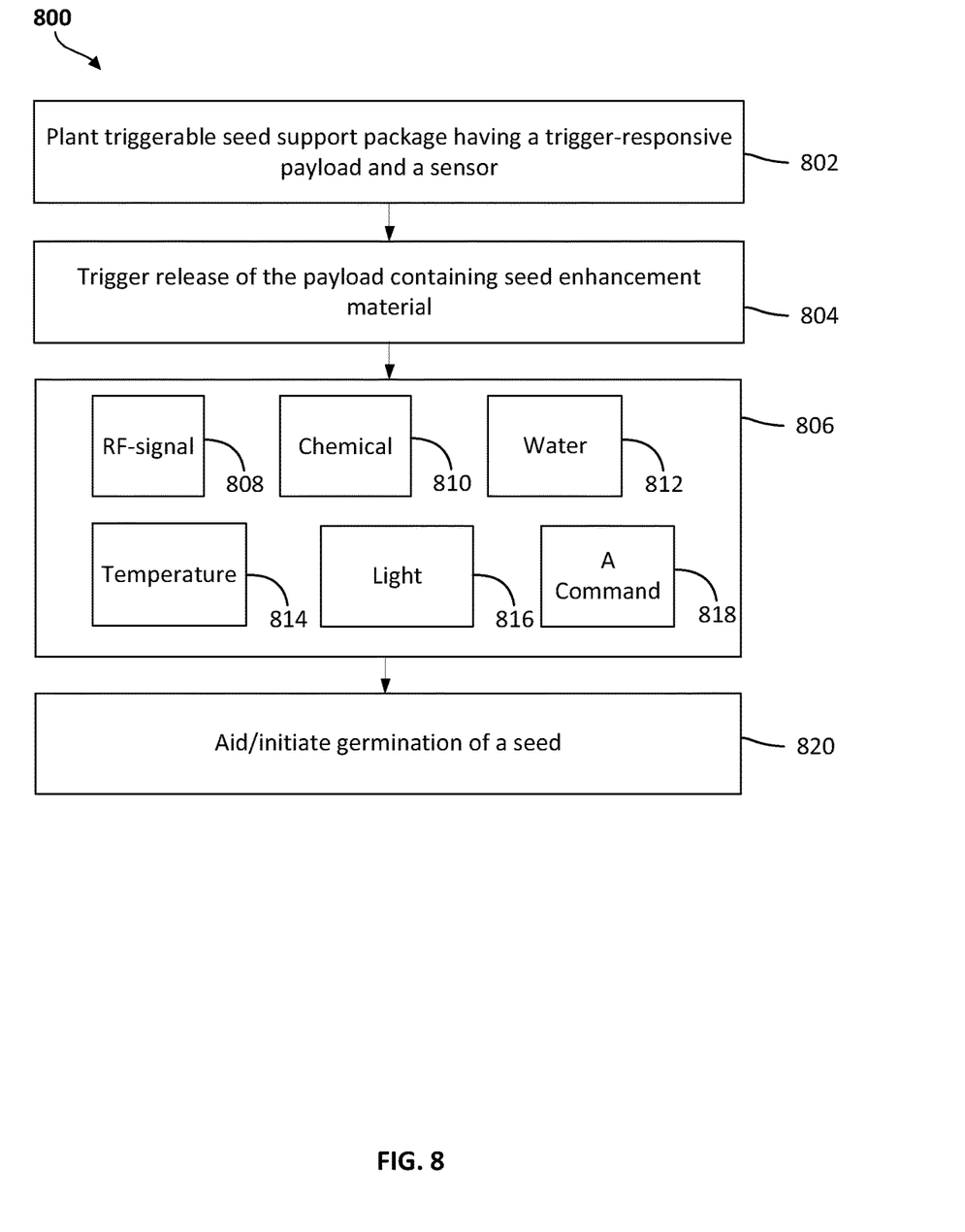
FIG. 8 is a flowchart of a process for enhancing crop production according to one embodiment.

Referring to FIG. 8, a flow diagram of a process 800 for enhancing crop production is shown, according to one embodiment. In alternative embodiments, fewer, additional, and/or different actions may be performed. A triggerable seed support package having a trigger-responsive payload and sensor is planted (802). The sensor may include any combination of sensors as described herein and the payload of the seed support package is triggered to release seed enhancement material (804) based on data provided by the sensor. The trigger may include a radiofrequency signal (808), a chemical (810), moisture (812), a temperature (814), light (816), or a command (e.g., encoded in a radiofrequency signal, etc.) (818). The released seed enhancement material aids or initiates germination of a seed (820).

Figure 9:
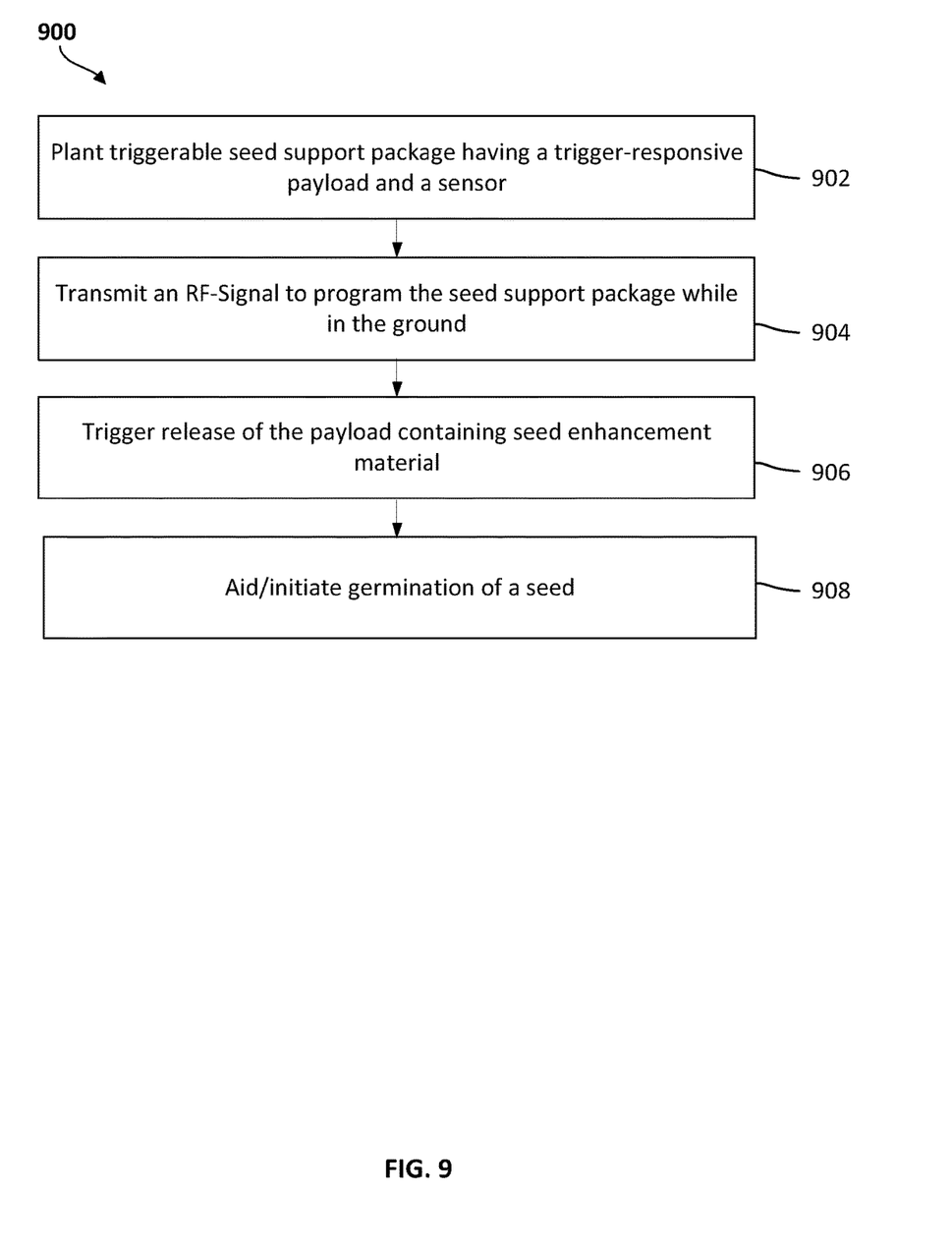
FIG. 9 is a flowchart of a process for enhancing crop production according to one embodiment.

Referring to FIG. 9, a flow diagram of a process 900 for enhancing crop production is shown, according to one embodiment. A triggerable seed support package having a trigger-responsive payload and sensor is planted (902). The sensor includes a radiofrequency sensor, and may further include any other combination of sensors as described herein. A radiofrequency signal is transmitted over the area of the seed support package. The signal includes instructions to program the triggering condition (e.g., define a valid trigger stored in configuration data 412) of the seed support package while the seed support package is in the ground (904). The payload of the seed support package is triggered to release seed enhancement material based on data provided by the sensor and the programmed triggering condition (906). The released seed enhancement material aids or initiates germination of a seed (908).

Figure 10:
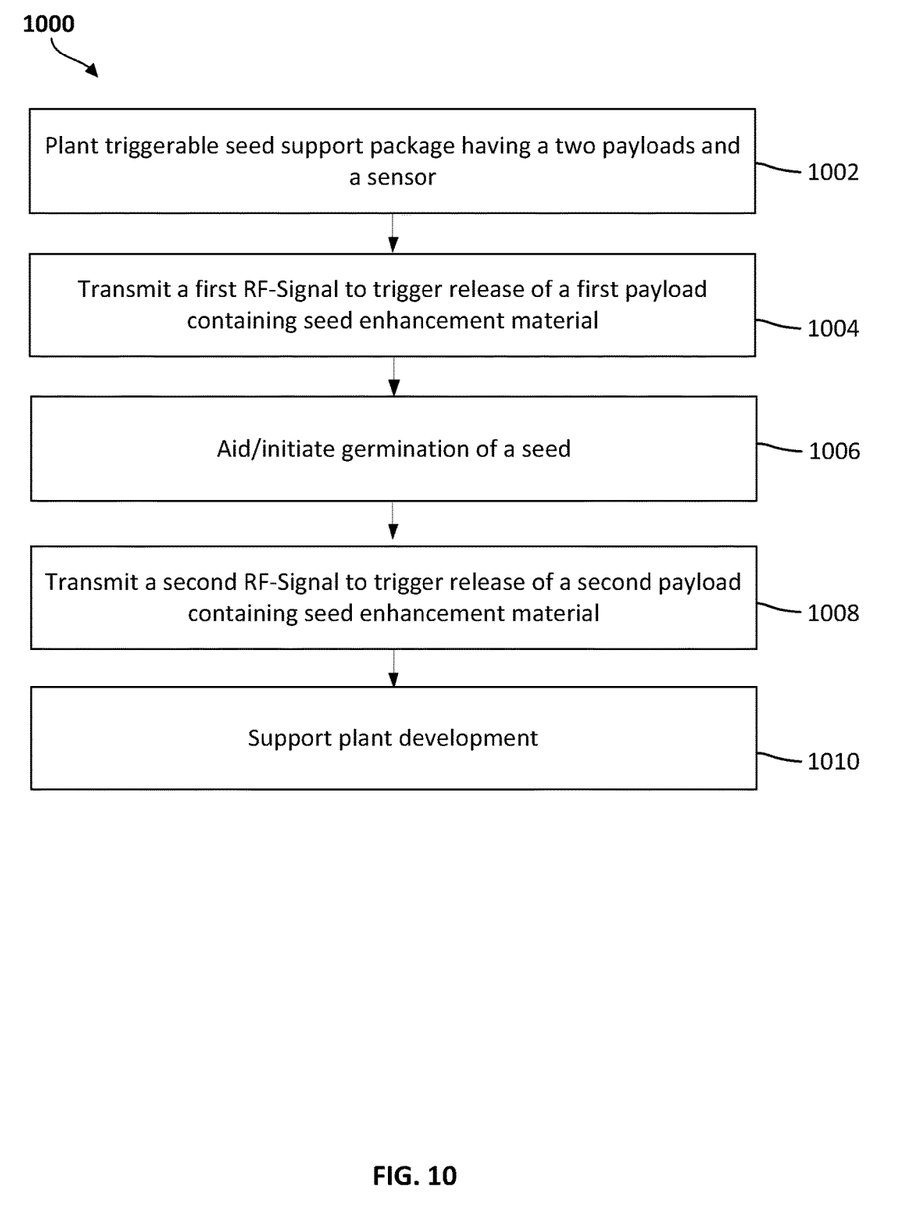
FIG. 10 is a flowchart of a process for enhancing crop production according to one embodiment.

Referring to FIG. 10, a flow diagram of a process 1000 for enhancing crop production is shown, according to one embodiment. A triggerable seed support package having two payloads and a sensor is planted (1002). The triggerable seed support package is configured to respond to a radiofrequency signal, and the payloads may each have a trigger corresponding to a different signal. A radiofrequency signal corresponding the first payload's trigger is transmitted to cause the release of the first payload containing seed enhancement material (1004). The released seed enhancement material of the first payload aids or initiates germination of a seed (1006). A radiofrequency signal corresponding the second payload trigger is transmitted to cause the release of the second payload containing seed enhancement material (1008). The released seed enhancement material of the second supports plant development of previously germinated seed (1010).

Figure 11:
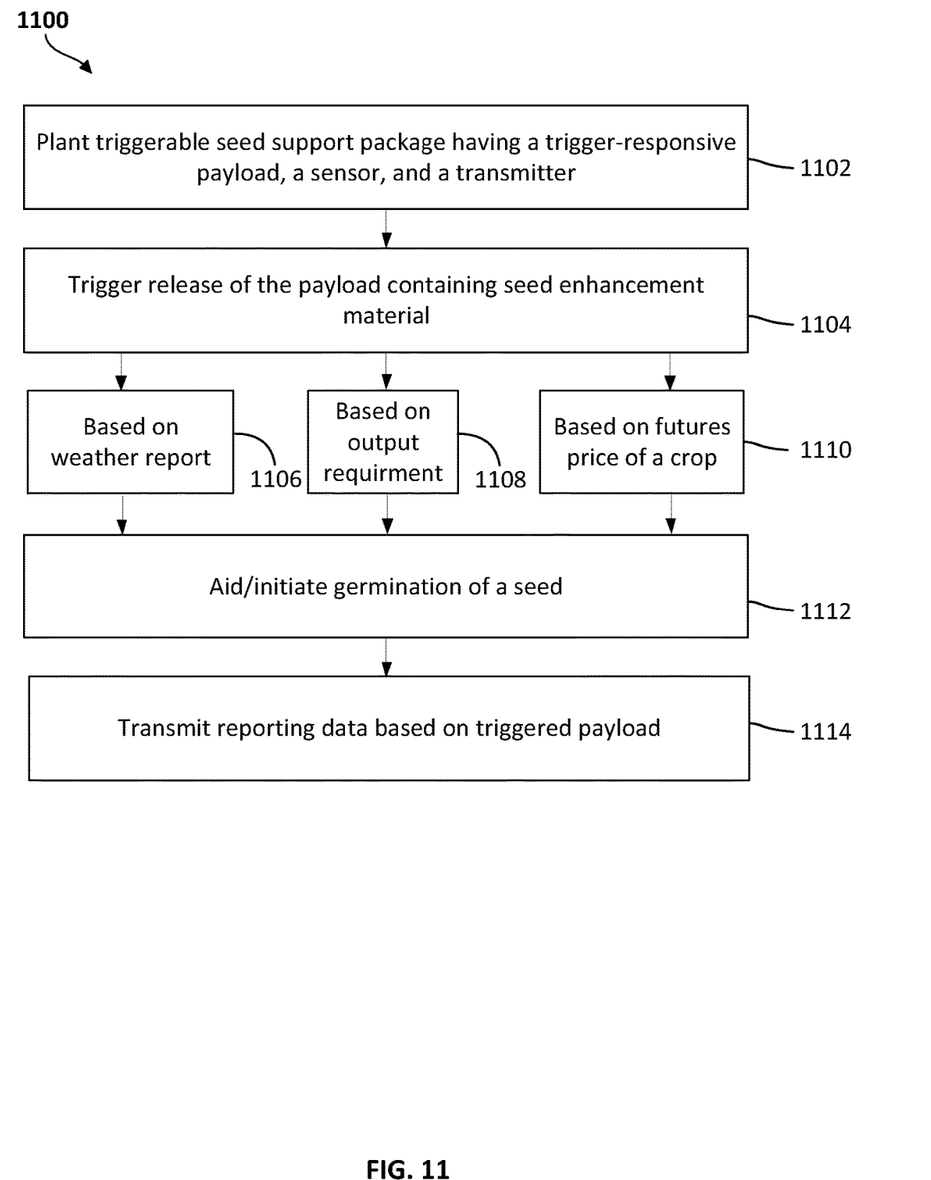
FIG. 11 is a flowchart of a process for enhancing crop production according to one embodiment.

Referring to FIG. 11, a flow diagram of a process 1100 for enhancing crop production is shown, according to one embodiment. A triggerable seed support package having a payload containing seed enhancement material, a sensor, and transmitter is planted (1102). The payload of the seed support package is triggered to release seed enhancement material (1104). The payload may be triggered based on an external condition, for example, a weather report (1106), an output or production requirement (1108), or a futures price of a crop (1110), etc. As an example, the payload of a seed support package of process 1100 may be triggerable based on a radiofrequency signal. Thus, based on the condition, a grower can actively trigger the release of seed enhancement material as he or she desires by transmitting the appropriate radiofrequency signal trigger. The released seed enhancement material from the payload aids or initiates germination of a seed (1112). The triggerable seed support package may transmit reporting data based on the triggered payload or the sensor data (1114).

The construction and arrangement of the systems and methods as shown in the various embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for enhancement of crop production, comprising:
   a triggerable seed support package comprising:
      a payload including seed enhancement material, wherein the payload is configured to be released in response to a trigger at least substantially synchronous with other seed support packages in a specific area of a crop.

2. The system of claim 1, wherein the seed support package includes a seed.

3. The system of claim 1, wherein the seed support package includes multiple seeds.

4. The system of claim 1, wherein the seed support package is configured to support an external seed.

5. The system of claim 1, wherein a packaging material of the seed support package is configured to enclose the payload.

6. The system of claim 1, wherein the seed enhancement material includes at least one of a micronutrient, a probiotic, a chemical, and a plant hormone.

7. The system of claim 1, wherein the trigger is configured to release the payload.

8. The system of claim 1, wherein the trigger is time-based.

9. The system of claim 8, wherein the trigger is a mechanical time-based trigger that is configured to cause a compartment of the seed support package to open to cause a release of the seed enhancement material at a specific time.

10. The system of claim 8, wherein the trigger is configured to cause a release of the seed enhancement material after a specific amount of time has elapsed.

11. The system of claim 1, wherein the trigger includes a fertilizer configured to penetrate the seed support package to thereby cause the release of the payload.

12. The system of claim 11, wherein the fertilizer is further configured to activate the seed enhancement material.

13. The system of claim 1, wherein packaging material of the seed support package is configured to be reactive to moisture, and wherein the trigger includes moisture in the soil.

* * * * *